United States Patent
Anzai (10) Patent No.: US 9,694,117 B2
(45) Date of Patent: Jul. 4, 2017

(54) ANTITHROMBOTIC MEDICAL MATERIALS AND MEDICAL APPARATUS USING THE SAME MATERIALS

(71) Applicant: TERUMO KABUSHIKI KAISHA, Shibuya-ku, Tokyo (JP)

(72) Inventor: Takao Anzai, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/627,351

(22) Filed: Feb. 20, 2015

(65) Prior Publication Data

US 2015/0238664 A1  Aug. 27, 2015

(30) Foreign Application Priority Data

Feb. 24, 2014 (JP) ................... 2014-033408

(51) Int. Cl.
*A61L 33/06* (2006.01)

(52) U.S. Cl.
CPC .................. *A61L 33/064* (2013.01)

(58) Field of Classification Search
CPC ........ A61L 33/064; A61L 33/06; A61L 33/00; A61L 33/0005
See application file for complete search history.

(56) References Cited

U.S. PATENT DOCUMENTS

2009/0124707 A1  5/2009  Tamori et al.
2014/0235748 A1*  8/2014  Haraguchi ............ A61L 33/064
                                                523/112

FOREIGN PATENT DOCUMENTS

JP  04-152952 A  5/1992
JP  2009-133809 A  6/2009

* cited by examiner

*Primary Examiner* — Robert A Wax
*Assistant Examiner* — Olga V Tcherkasskaya
(74) *Attorney, Agent, or Firm* — Buchanan Ingersoll & Rooney PC (57) ABSTRACT

A medical material that is excellent in antithrombogenicity even under a severe use condition in which thrombi are easily formed, is provided. The medical material contains a water-insoluble copolymer including a repeating unit (A) (which is derived from acryloylmorpholine, for example) and a repeating unit (B) (which is derived from methoxyethyl acrylate, for example), in which the water-insoluble copolymer has 5 mole % to 20 mole % of the repeating unit (A) with respect to all constituent units of the copolymer.

11 Claims, 2 Drawing Sheets

ANTITHROMBOTIC MEDICAL MATERIALS AND MEDICAL APPARATUS USING THE SAME MATERIALS

CROSS-REFERENCES TO RELATED APPLICATIONS

This application claims priority to Japanese Application No. 2014-033408 filed on Feb. 24, 2014, the entire content of which is incorporated herein by reference.

TECHNICAL

The present disclosure relates to an antithrombotic medical material and a medical apparatus using the medical material. More specifically, the present disclosure relates to a medical material containing a copolymer having a specific repeating unit, and a medical apparatus using the medical material.

BACKGROUND DISCUSSION

Recently, studies on medical materials utilizing various polymeric materials have been in progress and their application to membranes for an artificial kidney, membranes for a blood plasma separator, catheters, stents, membranes for an oxygenator, artificial blood vessels, membranes for preventing synechia, artificial skin, or the like is expected. In this case, synthetic polymeric materials that are foreign materials to living bodies are used in contact with biological tissues or body fluids such as blood. Accordingly, it can be desirable for the medical material to have biocompatibility. Although the biocompatibility required for the medical material varies depending on its purpose or usage, characteristics (antithrombogenicity) such as inhibition of a blood coagulation system, inhibition of adhesion and activation of platelets, and inhibition of activation of a complement system are expected as the medical material used as a material coming into contact with blood.

In general, imparting of the antithrombogenicity to a medical apparatus is performed through a method of coating a base material constituting the medical apparatus with an antithrombotic material, or a method of fixing the antithrombotic material onto the surface of the base material.

For example, JP-A-4-152952 discloses membranes for artificial organs or medical apparatuses of which the surfaces are provided with synthetic polymers simultaneously satisfying the biocompatibility such as inhibition of adhesion and activation of platelets and an effect of inhibition of activation of a complement system, and affinity for tissues in living bodies, and which are used in contact with tissues or blood in living bodies.

SUMMARY

According to an exemplary aspect, a medical material is provided, comprising:

a water-insoluble copolymer comprising:

a repeating unit (A) represented by the following Formula (1):

wherein in Formula (1), $R^{11}$ is a hydrogen atom or a methyl group and X is represented by the following Formula (1a):

wherein in Formula (1a), $R^{12}$ and $R^{13}$ each independently represent an alkylene group having 1 to 4 carbon atoms and Y is an oxygen atom, a sulfur atom, or a single bond; and a repeating unit (B) represented by the following Formula (2):

wherein in Formula (2), $R^{21}$ is a hydrogen atom or a methyl group, $R^{22}$ is an alkylene group having 1 to 4 carbon atoms, and $R^{23}$ is an alkyl group having 1 to 4 carbon atoms, wherein the water-insoluble copolymer has 5 mole % to 20 mole % of the repeating unit (A) with respect to all constituent units of the copolymer.

According to another exemplary aspect, a medical apparatus is provided, comprising: a base material; and a coating layer containing an exemplary medical material on the surface of the base material.

BRIEF DESCRIPTION OF DRAWINGS

FIG. 1 is a tube (stepped tube) which is used in Examples and of which both ends are connected using a connector, according to an exemplary aspect. In FIG. 1, the portion surrounded by a circle shows a joint portion between a tube 1 and a tube 2.

DETAILED DESCRIPTION

In medical apparatuses, such as artificial blood vessels or artificial organs, coming into contact with blood over a long period of time, antithrombogenicity for preventing blood coagulation is extremely important. However, in medical apparatuses having a step (stepped surface) on a surface coming into contact with blood, blood flow is obstructed in the portion (stepped portion) having the stepped surface, and therefore, there is a tendency that thrombi are easily formed in the periphery of the stepped portion. For example, in a blood flow path of a medical apparatus, blood flow is easily obstructed in the periphery of a throttle portion such as a joint portion of a tube used in the medical apparatus, and therefore, thrombi are comparatively easily formed.

A favorable result in view of the inhibition of the adhesion and activation of platelets is shown in the membrane disclosed in JP-A-4-152952. However, for example, under the severe conditions in which thrombi are comparatively easily formed as described above, in some cases, the antithrombogenicity does not sufficiently work in the membrane disclosed in JP-A-4-152952.

Accordingly, the disclosure has been made in consideration of the aforesaid circumstances. Provided is a medical material in which the antithrombogenicity is improved under severe conditions where thrombi are easily formed.

The aforesaid problem can be ameliorated or solved using a medical material which contains a water-insoluble copolymer having a specific repeating unit at a predetermined proportion. Disclosed are the following:

(1) A medical material which contains a water-insoluble copolymer comprising a repeating unit (A) represented by the following Formula (1)

(in Formula (1), $R^{11}$ is a hydrogen atom or a methyl group and X is represented by the following Formula (1a))

(in Formula (1a), $R^{12}$ and $R^{13}$ each independently represent an alkylene group having 1 to 4 carbon atoms and Y is an oxygen atom, a sulfur atom, or a single bond) and a repeating unit (B) represented by the following Formula (2)

(in Formula (2), $R^{21}$ is a hydrogen atom or a methyl group, $R^{22}$ is an alkylene group having 1 to 4 carbon atoms, and $R^{23}$ is an alkyl group having 1 to 4 carbon atoms). The water-insoluble copolymer has 5 mole % to 20 mole % of the repeating unit (A) in all constituent units.

(2) The medical material according to (1), in which the copolymer has 80 mole % to 95 mole % of the repeating unit (B) in all constituent units (the total amount of the repeating unit (A) and the repeating unit (B) being 100 mole %).

(3) The medical material according to (1) or (2), in which, in Formula (1a), $R^{12}$ and $R^{13}$ are ethylene groups.

(4) The medical material according to any one of (1) to (3), in which in Formula (1a), Y is an oxygen atom.

(5) A medical apparatus including: a base material; and a coating layer containing the medical material according to any one of (1) to (4) on the surface of the base material.

According to the present disclosure, it is possible to provide a medical material exhibiting excellent antithrombogenicity even in a particular case where the medical material is used under severe conditions in which thrombi are easily formed.

The present disclosure relates to a medical material which contains a water-insoluble copolymer having a specific repeating unit at a predetermined proportion, and a medical apparatus using the medical material.

Hereinafter, embodiments of the present disclosure will be described. The present disclosure is not limited to the following embodiments. In addition, in some cases, the dimension ratio of the drawings is exaggerated for convenience of explanation and is different from the actual ratio.

In addition, in the present disclosure, "X to Y" showing a range means "greater than or equal to X and less than or equal to Y", and "weight" and "mass", "wt %" and "mass %", and "parts by weight" and "parts by mass" are respectively treated as synonyms. In addition, the measurement of an operation, physical properties, and the like is performed under conditions of room temperature (20° C. to 25° C.) and relative humidity of 40% to 50% unless otherwise specified.

Copolymer

The medical material according to the present disclosure contains a water-insoluble copolymer having a repeating unit (A) represented by the following Formula (1) and a repeating unit (B) represented by the following Formula (2).

Formula (1):

In Formula (1), $R^{11}$ is a hydrogen atom or a methyl group and a hydrogen atom is exemplary. In Formula (1), X is represented by the following Formula (1a).

(1a)

In Formula (1a), $R^{12}$ and $R^{13}$ each independently represent a straight or branched-chain alkylene group having 1 to 4 carbon atoms. It is exemplary that $R^{12}$ and $R^{13}$ each independently represent a straight or branched-chain alkylene group having 2 to 3 carbon atoms. Specific examples thereof include a methylene group, an ethylene group, a trimethylene group, a propylene group, and a tetramethylene group. Among these, it is exemplary that $R^{12}$ and $R^{13}$ be ethylene groups in consideration of the effect of improving the antithrombogenicity.

In Formula (1a), Y is an oxygen atom, a sulfur atom, or a single bond. It is exemplary that Y be an oxygen atom or a sulfur atom. It is exemplary that Y be an oxygen atom in view of antithrombogenicity.

Formula (2):

(2)

In Formula (2), $R^{21}$ is a hydrogen atom or a methyl group, for example, a hydrogen atom.

In Formula (2), $R^{22}$ is a cyclic, straight-chain, or branched-chain alkylene group having 1 to 4 carbon atoms, for example, a straight or branched-chain alkylene group having 1 to 4 carbon atoms. Specific examples thereof include a methylene group, an ethylene group, a trimethylene group, a propylene group, a cyclopropylene group, a tetramethylene group, and a cyclobutylene group. Among these, in consideration of the effect of improving the antithrombogenicity, a straight or branched-chain alkylene group having 1 to 3 carbon atoms is exemplary and a methylene group or an ethylene group is exemplary.

In Formula (2), $R^{23}$ is a cyclic, straight-chain, or branched-chain alkyl group having 1 to 4 carbon atoms, for example, a straight or branched-chain alkyl group having 1 to 4 carbon atoms. Specific examples thereof include a methyl group, an ethyl group, a propyl group, an isopropyl group, an n-butyl, a sec-butyl, a tert-butyl group, and a cyclopropyl group. Among these, in consideration of the effect of improving the antithrombogenicity, a straight or branched-chain alkyl group having 1 to 3 carbon atoms is exemplary, a methyl group or an ethyl group is exemplary, and a methyl group is exemplary.

The copolymer contained in the medical material according to the present disclosure can be obtained by a polymerization reaction between a monomer forming the repeating unit (A) (hereinafter, referred to as a "monomer a") and a monomer forming the repeating unit (B) (hereinafter, referred to as a "monomer b").

Examples of the monomer a include acryloyl morpholine (4-acryloyl morpholine, ACMO), 4-acryloyl thiomorpholine, 1-acryloyl pyrrolidine, 1-acryloyl piperidine, 4-methacryloyl morpholine, 4-methacryloyl thiomorpholine, 1-methacryloyl pyrrolidine, and 1-methacryloyl piperidine, for example, acryloyl morpholine, 4-acryloyl thiomorpholine, 4-methacryloyl morpholine, and/or 4-methacryloyl thiomorpholine, for example, acryloyl morpholine. These monomers can be used alone or two or more thereof can be used in combination. It is possible to impart high antithrombogenicity to the medical material using acryloyl morpholine (ACMO).

Examples of the monomer b include methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate. Examples of the monomer b include methoxymethyl acrylate, methoxyethyl acrylate (MEA), ethoxymethyl acrylate, ethoxyethyl acrylate, methoxymethyl methacrylate, methoxyethyl methacrylate, ethoxymethyl methacrylate, and ethoxyethyl methacrylate. Examples thereof include methoxyethyl acrylate (MEA) in view of being easily available. These monomers can be used alone or two or more thereof can be used in combination.

The copolymer contained in the medical material according to the present disclosure may have 5 mole % to 20 mole % of a repeating unit (A) in all constituent units (100 mole %), for example, 6 mole % to 19 mole % therein. Here, the repeating unit (A) has high hydrophilicity, and when being contained in a copolymer at a moderate proportion, the copolymer shows favorable antithrombogenicity. In contrast, there are concerns that water solubility of the copolymer may become high when the repeating unit (A) is contained therein in a too large proportion, and an antithrombotic material may peel off when the antithrombotic material is applied to a medical apparatus.

When the repeating unit (A) exists in all constituent units of the copolymer in a proportion less than 5 mole %, it is impossible to obtain a sufficient effect of improving antithrombogenicity and thrombi are formed in a severe environment in which a medical apparatus is used over a long period of time under conditions where thrombi are easily formed. In contrast, when the repeating unit (A) exists in a proportion greater than 20 mole %, there is a risk that the antithrombotic material coated on a medical apparatus may peel off from a base material and may be liquated (mixed) into body fluids (for example, blood) when the medical apparatus comes into contact with the body fluids, due to an action of imparting of water solubility by the repeating unit (A).

The copolymer can have 80 mole % to 95 mole % of a repeating unit (B) in all constituent units, for example, 81 mole % to 94 mole % thereof in all constituent units.

The copolymer contained in the medical material according to the present disclosure is excellent in antithrombogenicity. The technical range of the present disclosure is not limited, but the mechanism is as follows. That is, it is considered that a copolymer having a constituent unit (A) has excellent hydrophilicity compared to a polymer only formed of a constituent unit (B), biocompatibility becomes high by applying a medical material, which contains such a copolymer provided with the moderate hydrophilicity, to a medical apparatus, and formation of thrombi is suppressed even in a case in which the medical apparatus is used under a condition where thrombi are easily formed. Note that the present disclosure is not limited to the above-described mechanism.

In another embodiment, a copolymer contained in the medical material of the present disclosure is a water-insoluble copolymer of monomer a, monomer b, and another monomer which is copolymerizable with these (hereinafter, also simply referred to as "another monomer").

Examples of the another monomer which is copolymerizable with the monomer a and the monomer b include acrylamide, N,N-dimethylacrylamide, N,N-diethyl acrylamide, N-vinylacetamide, sulfobetaine methacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethyl methacrylamide, N,N-diethyl methacrylamide, aminomethyl methacrylate, aminoethyl methacrylate, diaminomethyl methacrylate, diaminoethyl methacrylate, methyl acrylate, ethyl acrylate, isopropyl acrylate, butyl acrylate, 2-ethylhexyl acrylate, methyl methacrylate, ethyl methacrylate, butyl methacrylate, hexyl acrylate, hexyl methacrylate, carboxybetaine methacrylate, ethylene, and propylene.

The proportion of a repeating unit, which is derived from another monomer, in all constituent units of the copolymer is, for example, greater than 0 mole % and less than or equal to 15 mole %, and, for example, greater than 0 mole % and less than or equal to 13 mole %.

In the copolymer, the proportion of the repeating unit (A), repeating unit (B), or the repeating unit derived from another monomer can be arbitrarily adjusted by changing the proportion of the monomer used during polymerization.

In an embodiment of the present disclosure, the copolymer contained in the medical material is constituted of a repeating unit (A) and a repeating unit (B). That is, in the embodiment of the present disclosure, the copolymer has 5 mole % to 20 mole % of the repeating unit (A) in all constituent units and 80 mole % to 95 mole % of the repeating unit (B) in all constituent units (the total amount of the repeating unit (A) and the repeating unit (B) is 100 mole %). In another embodiment, the copolymer contained in the medical material has 6 mole % to 19 mole % of the repeating unit (A) in all constituent units and 81 mole % to 94 mole % of the repeating unit (B) in all constituent units (the total amount of the repeating unit (A) and the repeating unit (B) is 100 mole %).

The copolymer contained in the medical material of the present disclosure is water-insoluble. In the present specification, the "water insolubility" refers to a case in which the solubility in water at 25° C. is less than 1 wt %. For example, a water-insoluble copolymer can prevent a medical material from being mixed or liquated into body fluids that pass through a tube of a medical apparatus. JP-A-2009-133809 discloses a nonspecific adsorption inhibitor of a bio-related material which contains a copolymer having a predetermined repeating unit. However, the copolymer disclosed in the document is water-soluble, has different physical properties from that of the water-insoluble copolymer contained in the present disclosure, and has different applications depending on the physical properties. In the present disclosure, it is possible to obtain the water-insoluble copolymer by setting the proportion of the hydrophilic repeating unit (A) in the entire copolymer to be less than or equal to 20 mole %.

In the present disclosure, the solubility of the copolymer in water is, for example, less than 1 wt %, for example, less than 0.1 wt %. The lower limit value of the solubility in water is not limited, but examples thereof include 0 wt %. The solubility of the copolymer in water is, specifically, measured through a method described in Examples.

The terminal of the copolymer contained in the medical material of the present disclosure is not particularly limited and can be appropriately defined by the type of raw materials used, and is generally a hydrogen atom. The structure of the copolymer is also not particularly limited and may be any one of a random copolymer, an alternating copolymer, a periodic copolymer, and a block copolymer.

The weight-average molecular weight of the copolymer can be 10000 to 1000000. It is exemplary that the weight-average molecular weight of the copolymer be in the above-described range in view of solubility. The weight-average molecular weight of the copolymer is, for example, 30000 to 500000 in view of easy coating of a coating layer. In the present disclosure, the "weight-average molecular weight" employs a value measured through gel permeation chromatography (GPC) using polystyrene as a reference material.

The method of producing the copolymer contained in the medical material according to the present disclosure is not particularly limited. For example, well-known polymerization methods such as radical polymerization, anionic polymerization, and cationic polymerization can be employed, and, for example, radical polymerization is used in view of easy production. A plasma polymerization method using a radiation ray or an ultraviolet ray is employed as the method of producing the copolymer contained in the medical material according to the present disclosure, and a coating layer containing the copolymer may be formed on a surface of a base material.

As the polymerization method of the monomer, in general, a copolymerization method of stirring and heating one or two kinds of the monomers a (for example, acryloylmorpholine (ACMO)) corresponding to the aforesaid repeating unit (A) and one or more kinds of the aforesaid monomers b (for example, methoxyethyl acrylate (MEA)) corresponding to the aforesaid repeating unit (B), and another monomer as desired, together with a polymerization initiator in a polymerization solvent can be used.

The polymerization temperature is, for example, 40° C. to 120° C. in view of controlling the molecular weight. The polymerization reaction is generally performed for 30 minutes to 24 hours.

Examples of the polymerization solvent include non-proton-donating solvents such as toluene, xylene, diethyl ether, chloroform, ethyl acetate, methylene chloride, tetrahydrofuran, acetone, acetonitrile, N,N-dimethylformamide, and dimethyl sulfoxide; alcohols such as methanol, ethanol, propanol, and n-butanol; and polyhydric alcohols such as ethylene glycol, diethylene glycol, propylene glycol, and dipropylene glycol, and toluene is particularly exemplary. These may be used alone or two or more thereof may be used in combination.

The monomer concentration (solid content concentration) in a polymerization solvent is generally 5 wt % to 90 wt % with respect to the entire reaction solution and, for example, 10 wt % to 80 wt % with respect to the entire reaction solution. Note that the monomer concentration with respect to the polymerization solvent indicates a concentration of total weight of a monomer a, a monomer b, and another monomer which is arbitrarily contained and is copolymerizable with these (hereinafter, "a monomer a, a monomer b, and another monomer which is arbitrarily contained and is copolymerizable with these" is also referred to as a "polymerization monomer").

The polymerization solvent to which a polymerization monomer is added may be subjected to deaeration treatment before adding a polymerization initiator thereto. For the deaeration treatment, for example, the polymerization solvent to which a polymerization monomer is added may be bubbled for 0.5 hours to 5 hours using inert gas such as nitrogen gas or argon gas. During the deaeration treatment, the polymerization solvent to which a polymerization monomer is added may be heated to, approximately, 40° C. to 120° C.

A well-known polymerization initiator can be used for producing the copolymer and is not particularly limited, but examples thereof include azo-based polymerization initiators such as 2,2'-azobisisobutyronitrile, 2,2'-azobis(4-methoxy-2,4-dimethylvaleronitrile), and 2,2'-azobis(2,4-dimethylvaleronitrile); and redox-based polymerization initiators in which reducing agents such as sodium sulfite, sodium hydrogen sulfite, or ascorbic acid is combined with oxidants for example, persulphates such as potassium persulphate (KPS), sodium persulphate, or ammonium persulphate, or peroxides such as hydrogen peroxide, t-butyl peroxide, or methyl ethyl ketone peroxide.

The blending amount of the polymerization initiator is, for example, 0.0001 moles to 1 mole with respect to the entire polymerization monomer (1 mole) used for producing the copolymer.

Furthermore, if desired, a chain transfer agent, a polymerization rate modifier, a surfactant, and other additives may be appropriately used during the polymerization.

The atmosphere in which the polymerization reaction is performed is not particularly limited, and the polymerization reaction can be performed in an air atmosphere, an inert gas atmosphere such as nitrogen gas or argon gas, and the like. In addition, the reaction solution may be stirred during the polymerization reaction.

The copolymer after polymerization can be purified through general purification methods such as re-precipitation, dialysis, ultrafiltration, and extraction.

The copolymer after purification can be dried through an arbitrary method such as freezing and drying, drying under reduced pressure, spray drying, and heating and drying, and freezing and drying or drying under reduced pressure is exemplary in view of a small influence on physical properties of a polymer.

The proportion of a repeating unit (A), a repeating unit (B), or a repeating unit derived from another monomer, in the obtained copolymer may be confirmed through an NMR method, infrared ray spectral analysis, and the like. For example, in a case of a copolymer constituted of a repeating unit (A) and a repeating unit (B), the proportion of the repeating unit (A) to the repeating unit (B) in the copolymer can be analyzed using an integration proportion in 1HNMR measurement.

An unreacted polymerization monomer which is contained in the obtained copolymer is, for example, less than or equal to 0.01 wt % with respect to the entire copolymer. It is exemplary that the unreacted polymerization monomer be as small as possible, and therefore, there is no particular limitation for the lower limit, but an example thereof includes 0 wt %. The content of the residual monomer can be measured through methods, such as high-speed liquid chromatography, known to those skilled in the art.

The medical material in the present disclosure may be used in a form constituted of the obtained copolymer and can also be used by being processed in a gel state, a solution state, or the like by being combined with a gelling agent, a thickener, a plasticizer, a solvent, or the like. For example, the medical material can be used in a form of a coating agent in which the copolymer is dissolved in a solvent.

When the medical material is used in the form of the coating agent, there is no limitation for the solvent to be used as long as the copolymer can be dissolved therein, but examples thereof include toluene, xylene, diethyl ether, chloroform, ethyl acetate, methylene chloride, tetrahydrofuran, acetone, acetonitrile, N,N-dimethylformamide, dimethyl sulfoxide, methanol, ethanol, propanol, n-butanol, ethylene glycol, diethylene glycol, propylene glycol, and dipropylene glycol. The aforesaid solvent may be used alone or two or more thereof may be used in combination.

The amount of the copolymer contained in the coating agent can be arbitrarily set and the coating agent can be used as a solution in which the copolymer is dissolved to the saturated amount. For example, the amount of the copolymer is 0.1 wt % to 50 wt % with respect to the entire coating agent.

The coating agent may be constituted of the copolymer and the aforesaid solvent and may also arbitrarily contain other components such as a cross-linking agent, a thickener, a preservative, and a pH adjusting agent. The copolymer can be more firmly fixed onto the surface of a base material by including the cross-linking agent.

In an embodiment of the present disclosure, a medical apparatus using the aforesaid medical material is provided. That is, in the embodiment of the present disclosure, a medical apparatus, which has a base material, and a coating layer containing the aforesaid medical material on the surface of the base material, is provided.

Examples of the medical apparatus according to the present disclosure include intracorporeal embedment type artificial organs or treatment instruments, extracorporeal circulation type artificial organs, catheters, and guide wires. Specific examples thereof include embedment type medical instruments such as artificial blood vessels which are inserted into or substituted with blood vessels or lumens, an artificial trachea, a stent, an artificial skin, and an artificial pericardium; artificial organ systems such as an artificial heart system, an oxygenator system, an artificial cardiopulmonary system, an artificial kidney system, an artificial liver system, and an immunomodulatory system; catheters which are inserted into or indwelled in blood vessels, for example, an indwelling needle, an IVH catheter, a catheter for administering a drug solution, a thermodilution catheter, a catheter for angiography, a catheter and a dilator for vasodilation, and an introducer; a guide wire or a stilet for these catheters, or the like; catheters which are inserted into or indwelled in biological tissues other than blood vessels, for example, a nasogastric tube catheter, a nutrition catheter, a tube for tube feeding (ED), a urethral catheter, a urinary catheter, a balloon catheter, various suction catheters including an endotracheal suction catheter, and a drainage catheter. In particular, the medical apparatus is suitably used in an oxygenator system or an artificial cardiopulmonary system coming into contact with a large amount of blood.

The medical apparatus according to the present disclosure has the aforesaid medical material on the surface of a base material. Examples of the material which constitutes the base material are not particularly limited and examples thereof include polyolefin or modified polyolefin such as polyethylene, polypropylene, ethylene-α-olefin copolymer; polyamide; polyimide; polyurethane; polyesters such as polyethylene terephthalate (PET), polybutylene terephthalate (PBT), polycyclohexane terephthalate, polyethylene-2,6-naphthalate; polyvinyl chloride; polyvinylidene chloride (PVDC); various polymeric materials such as fluorine resins such as polytetrafluoroethylene (PTFE), and ethylene-tetrafluoroethylene copolymer (ETFE); metals; ceramics; carbons; and composite materials thereof.

The shape of the base material can be appropriately selected in accordance with the application of the medical apparatus, and examples thereof include a tube shape, a sheet shape, and a rod shape. The form of the base material is not limited to a molded body singly using the aforesaid material, and a blended molded product, an alloyed molded product, and a multilayered molded product can also be used. The base material may be single layered or may be multilayered. At this time, in a case where the base material is multilayered, the base materials of the layers may be the same as or be different from each other. However, when a copolymer is to be firmly fixed by swelling the base material with a solvent, the aforesaid polymeric material can be favorably swollen using the solvent, and therefore, the polymeric material is exemplary as the material existing at least on the surface of the base material.

In the present disclosure, the "surface of the base material" is a surface of a base material which faces biological tissues or body fluids such as blood. Antithrombogenicity of the surface of the base material is improved by forming a coating layer containing a copolymer on the surface of the base material. In the medical apparatus according to the present disclosure, the coating layer containing a copolymer may be formed on the surface of the base material which faces biological tissues or body fluids such as blood, but this does not preclude formation of the coating layer on other surfaces.

The base material may be subjected to surface treatment before forming the coating layer on the surface of the base material in order to improve stability of the coating layer on the surface of the base material. Examples of the surface treatment method of the base material include a method of radiating active energy rays (an electron beam, an ultraviolet ray, an X-ray, and the like), a method of using plasma discharges such as an arc discharge, a corona discharge, and a glow discharge, a method of applying a high electric field, a method of applying ultrasonic vibration through a polar liquid (water or the like), and a method of performing treatment using ozone gas.

In the medical apparatus according to the present disclosure, a coating layer containing the aforesaid medical material is formed on the surface of a base material.

The coating layer on the surface of the base material may be formed by applying coating liquid (for example, the aforesaid coating agent) containing the aforesaid medical material on the surface of the base material to be coated, or by performing plasma polymerization by applying a polymerization solvent containing a polymerization monomer on the surface of the base material as described above. It is exemplary that the coating layer be formed by coating the surface of the base material using the coating liquid containing the aforesaid medical material in view of easy production. Note that the "coating" includes not only a form in which the entire surface of the base material is completely covered by the coating layer, but also a form in which a portion of the surface of the base material is covered by a coating layer, that is, a form in which a coating layer is adhered to a portion of the surface of the base material.

When forming a coating layer by coating the surface of the base material using the coating liquid containing the medical material, the aforesaid method of preparing the coating agent is appropriately considered for a method of preparing the coating liquid containing the medical material.

Well-known methods can be employed as the method of applying the coating liquid containing the medical material on the surface of the base material, and there is no particular limitation. Examples thereof include dip coating, spraying, spin coating, dropping, doctor blade, brush coating, roll coater, air knife coating, curtain coating, wire-bar coating, and gravure coating.

The thickness of the coating liquid may be appropriately adjusted depending on the application of the medical apparatus and there is no particular limitation. For example, the coating liquid is formed to be thinner than 0.1 μm.

The coating layer is formed on the surface of the base material by drying the surface of the base material applied with the coating liquid containing a copolymer. The drying process may be appropriately set in consideration of a glass transition temperature of the base material, or the like, and the temperature of the drying process is, for example, 15° C. to 50° C. The atmosphere in the drying process is not particularly limited, and the process can be performed in the air or in an inert gas atmosphere such as nitrogen gas or argon gas.

EXAMPLES

The exemplary effect of the present disclosure will be described using the following Examples and Comparative Examples. However, the technical scope of the present disclosure is not limited to the following Examples.

Example 1

Copolymer Between ACMO and MEA (Repeating Unit (A): 19 mole %)

16.00 g (122.9 mmol) of methoxyethyl acrylate (MEA) and 4.00 g (28.3 mmol) of acryloylmorpholine (ACMO) were dissolved in 80.0 g of toluene, the mixture was put into a four-necked flask, and then, $N_2$ bubbling was performed thereon for 1 hour at 80° C.

Then, a solution, in which 0.02 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 110000.

Example 2

Copolymer Between ACMO and MEA (Repeating Unit (A): 13 mole %)

16.00 g (122.9 mmol) of MEA and 2.50 g (17.7 mmol) of ACMO were dissolved in 74.0 g of toluene, the mixture was put into a four-necked flask, and then, N$_2$ bubbling was performed thereon for 1 hour at 80° C.

Then, a solution, in which 0.02 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 95000.

Example 3

Copolymer Between ACMO and MEA (Repeating Unit (A): 6 mole %)

9.00 g (69.2 mmol) of MEA and 0.65 g (4.6 mmol) of ACMO were dissolved in 38.6 g of toluene, the mixture was put into a four-necked flask, and then, N$_2$ bubbling was performed thereon for 1 hour at 80° C.

Then, a solution, in which 0.01 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 92000.

Comparative Example 1

Copolymer Between ACMO and MEA (Repeating Unit (A): 48 mole %)

9.00 g (69.2 mmol) of MEA and 9.00 g (63.8 mmol) of ACMO were dissolved in 72.0 g of toluene, the mixture was put into a four-necked flask, and then, N$_2$ bubbling was performed thereon for 1 hour at 80° C.

Then, a solution, in which 0.02 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 68000.

Comparative Example 2

Copolymer Between ACMO and MEA (Repeating Unit (A): 25 mole %)

14.00 g (107.6 mmol) of MEA and 5.00 g (35.4 mmol) of ACMO were dissolved in 76.0 g of toluene, the mixture was put into a four-necked flask, and then, N$_2$ bubbling was performed thereon for 1 hour at 80° C.

Then, a solution, in which 0.02 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 78000.

Comparative Example 3

Copolymer Between ACMO and MEA (Repeating Unit (A): 3 mole %)

9.00 g (69.2 mmol) of MEA and 0.30 g (2.1 mmol) of ACMO were dissolved in 37.2 g of toluene, the mixture was put into a four-necked flask, and then, N$_2$ bubbling was performed thereon for 1 hour at 80° C.

Then, a solution, in which 0.01 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited copolymer was collected. Note that the weight-average molecular weight of the collected copolymer was 55000.

Comparative Example 4

(Homo)Polymer of MEA (Repeating Unit (A): 0 mole %)

18.00 g (138.3 mmol) of MEA was dissolved in 72.0 g of toluene, the mixture was put into a four-necked flask, and then, N$_2$ bubbling was performed thereon for 1 hour at 80° C.

Then, a solution, in which 0.02 g of 2,2'-azobisisobutyronitrile (AIBN, manufactured by Wako Pure Chemical Industries, Ltd.) was dissolved in 1 mL of toluene, was added to toluene which was mixed with a polymerization monomer, and the mixture was polymerized for 5 hours at 80° C. The polymerization liquid was added dropwise to normal hexane and deposited polymer was collected. Note that the weight-average molecular weight of the collected polymer was 82000.

The aforesaid copolymer or polymer which was obtained in Examples or in Comparative Examples was purified through a reprecipiation method. Then, the copolymer or the polymer was dried through drying under reduced pressure and was subjected to the following tests.

Test Example 1

Solubility Test of Polymer (Copolymer or Polymer)

0.1 g of each of the aforesaid copolymers or polymers (hereinafter, the "copolymers or polymers" are also referred to as "polymers") which was obtained in Examples or in Comparative Examples was measured and collected, and each was put into a separate glass test tube.

5 g of a physiological salt solution was added to the aforesaid test tube and was stirred, and the solubility of the polymer was examined. In a case in which the polymer maintained its form at the time of being put into the glass test tube when visually observed, the polymer was regarded as being insoluble in the physiological salt solution. In a case in which there was no insoluble component or the polymer was dispersed while it was a bit cloudy, the polymer was regarded as being dissolved in the physiological salt solution.

TABLE 1

| | Solubility in physiological salt solution |
|---|---|
| Example 1 (MEA-ACMO copolymer) repeating unit (A): 19 mole % | Insoluble |
| Example 2 (MEA-ACMO copolymer) repeating unit (A): 13 mole % | Insoluble |
| Example 3 (MEA-ACMO copolymer) repeating unit (A): 6 mole % | Insoluble |
| Comparative Example 1 (MEA-ACMO copolymer) repeating unit (A): 48 mole % | Soluble |
| Comparative Example 2 (MEA-ACMO copolymer) repeating unit (A): 25 mole % | Soluble |

The result of Table 1 shows that the copolymer was not dissolved in the physiological salt solution if the repeating unit (A) in all constituent units of the copolymer is less than or equal to 20 mole % even if the copolymer contains the repeating unit (A) having high hydrophilicity.

From the result, it can be seen that a medical material can be appropriately coated on a medical apparatus if the repeating unit (A) in all constituent units of the copolymer is less than or equal to 20 mole % and that the medical material can be more efficiently prevented from peeling off from a base material and being mixed into blood.

Test Example 2

Solubility in Water 0.1 g of each of the polymers which was obtained in Examples or in Comparative Examples was measured and collected, and each was put into a separate glass test tube.

Distilled water was added to the aforesaid test tube and the total amount of the polymer and the distilled water was set to 10 g. The test tube was covered with a lid and was stirred, and then was allowed to stand for 24 hours at 25° C. to examine the solubility of the polymer. Evaluation of the solubility was performed similarly to Test Example 1 and the solubility of the polymer in water was evaluated from the result of the obtained solubility.

TABLE 2

| | Solubility in water (25° C.) (wt %) |
|---|---|
| Example 1 (MEA-ACMO copolymer) repeating unit (A): 19 mole % | Less than 1 wt % |
| Example 2 (MEA-ACMO copolymer) repeating unit (A): 13 mole % | Less than 1 wt % |
| Example 3 (MEA-ACMO copolymer) repeating unit (A): 6 mole % | Less than 1 wt % |
| Comparative Example 1 (MEA-ACMO copolymer) repeating unit (A): 48 mole % | Equal to or greater than 1 wt % |
| Comparative Example 2 (MEA-ACMO copolymer) repeating unit (A): 25 mole % | Equal to or greater than 1 wt % |

The solubility of polymers, which were obtained in Examples and Comparative Examples, in distilled water, was examined, and as a result, the polymers of Examples 1 to 3 maintained their forms from immediately after adding distilled water thereto, and therefore, the polymers were insoluble. In contrast, the polymers of Comparative Examples 1 and 2 were completely dissolved in the distilled water.

As shown in the aforesaid Table 2, the solubility of the copolymers according to Examples 1 to 3 in water is less than 1 wt %, which is insoluble. The water-insoluble copolymer can prevent a medical material from being mixed or liquated into liquids that pass through a tube of a medical apparatus, for example.

Test Example 3

Antithrombogenicity Test

Preparation of Coating Agent

A methanol solution was prepared as a coating agent with respect to each of the polymers obtained in Examples or Comparative Example such that the polymer concentration became 0.5 wt %.

Production of Medical Apparatus

End portions of a soft vinyl chloride tube (tube 2) having dimensions of full length 5 cm×inner diameter 6 mm×outer diameter 9 mm were inserted 1 cm into both ends of a soft vinyl chloride tube (tube 1) having a diameter of full length 30 cm×inner diameter 8 mm to produce a stepped tube.

Figure 1:
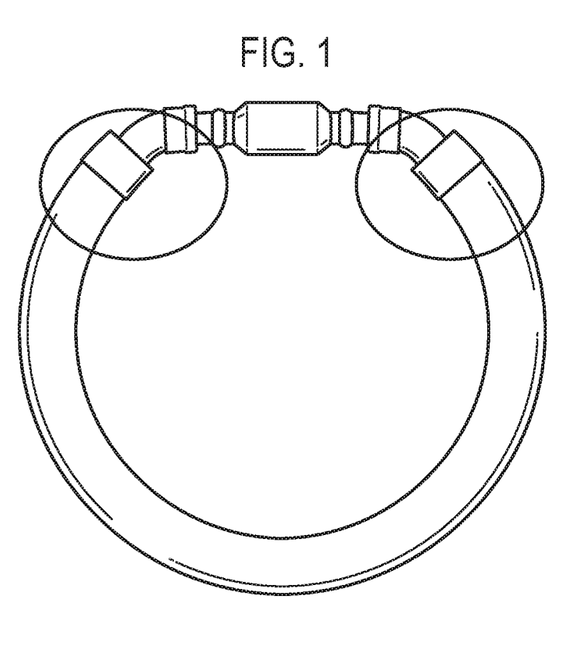

FIG. 1 is the produced stepped tube. In FIG. 1, the portion surrounded by a circle shows a joint portion between the tube 1 and the tube 2.

Figure 2:
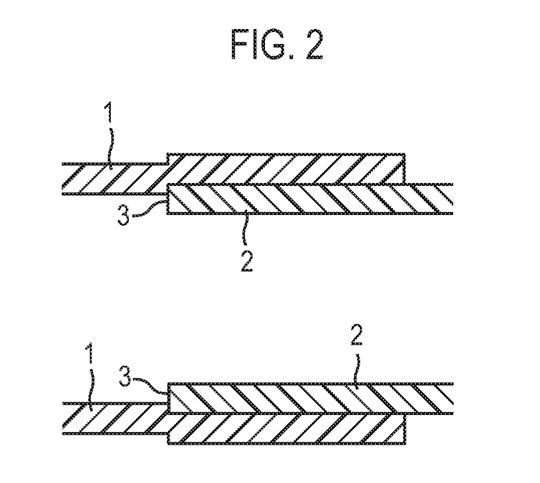
FIG. 2 is an enlarged view schematically showing a cross section in a long axis direction in the joint portion between the tube 1 and the tube 2 in FIG. 1, according to an exemplary aspect.

FIG. 2 is an enlarged view schematically showing the joint portion between the tube 1 and the tube 2 in FIG. 1. The inner diameter of the tube 2 is smaller than that of tube 1, and therefore, a stepped surface 3 is formed therebetween. When blood is passed through the stepped tube, thrombi are extremely easily formed on the stepped surface 3.

The aforesaid coating agent was passed through the stepped tube using the produced stepped tube as a base material to apply the coating agent on the surface of the base material. Then, the stepped tube was dried at room temperature (25° C.) to form a coating layer containing a medical material on the surface (surface of a lumen of the stepped tube) of the base material.

Antithrombogenicity Test

In order to evaluate antithrombogenicity of a medical material under severe conditions in which thrombi are easily formed, the following test system was established using the aforesaid stepped tube with a coating layer formed therein.

That is, the lumen of the aforesaid stepped tube with a coating layer formed therein was filled with 6 ml of liquid (diluted blood) in which fresh blood of a human was diluted twice in physiological salt solution. Both the ends of the stepped tube were connected to connectors and were fixed to a cylindrical rotating device, and the tube was rotated for 2 hours at 40 rpm. Then, circulating blood was removed from the stepped tube, and the state of thrombi being adhered to the joint portion (stepped surface) between the tube 1 and the tube 2 was visually observed. Here, the fresh blood refers to blood which has been collected from a donor of a healthy person through whole blood transfusion and is within 30 minutes after being collected. Note that no anticoagulant was added to the fresh blood.

Figure 3:
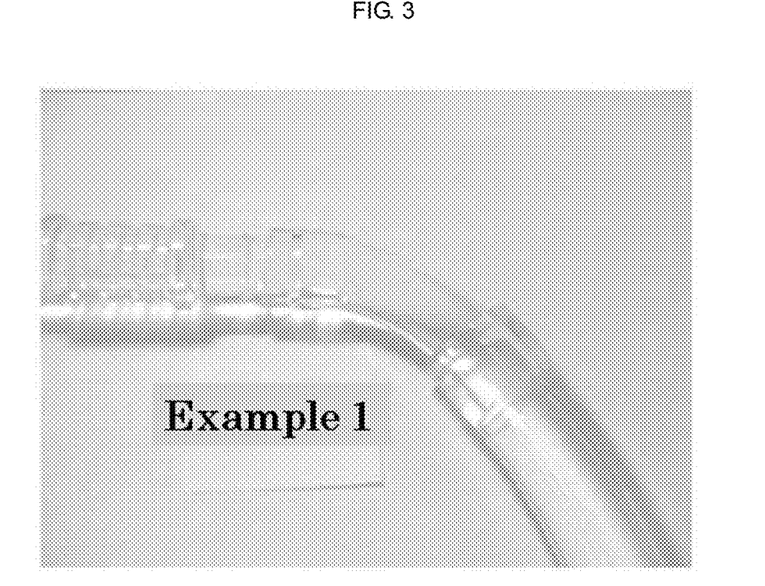
FIG. 3 is an enlarged photograph of the joint portion immediately after an antithrombogenicity test performed on a stepped tube to which a medical material containing a copolymer produced in Example 1 is applied, according to an exemplary aspect.
Figure 4:
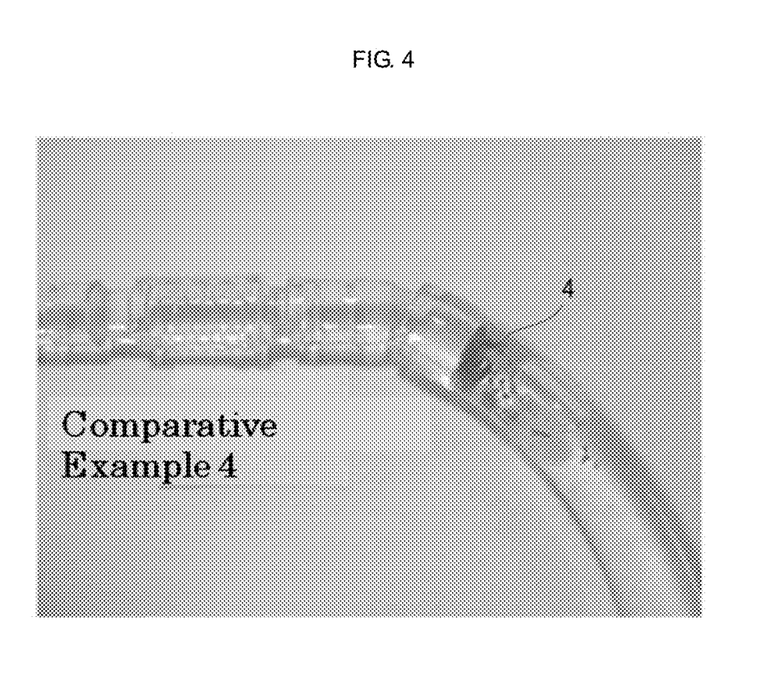
FIG. 4 is an enlarged photograph of the joint portion immediately after an antithrombogenicity test performed on a stepped tube to which a medical material containing a polymer produced in Comparative Example 4 is applied, according to an exemplary aspect.

FIG. 3 is an enlarged photograph of the joint portion immediately after testing the antithrombogenicity on a stepped tube to which a medical material containing the copolymer produced in Example 1 was applied, and FIG. 4 is an enlarged photograph of the joint portion immediately after testing the antithrombogenicity on a stepped tube to which a medical material containing the polymer produced in Comparative Example 4 was applied. No formation of thrombi was recognized in the stepped tube to which the medical material according to the present disclosure was applied (FIG. 3). In contrast, thrombi 4 were observed in the joint portion in the stepped tube to which the medical material containing the polymer of Comparative Example 4 was applied (FIG. 4). The result of the antithrombogenicity test is shown in Table 3.

TABLE 3

| | Formation of thrombi on stepped surface |
|---|---|
| Example 1 (MEA-ACMO copolymer) repeating unit (A): 19 mole % | None |
| Example 2 (MEA-ACMO copolymer) repeating unit (A): 13 mole % | None |
| Example 3 (MEA-ACMO copolymer) repeating unit (A): 6 mole % | None |
| Comparative Example 3 (MEA-ACMO copolymer) repeating unit (A): 3 mole % | Present |
| Comparative Example 4 (MEA polymer) repeating unit (A): 0 mole % | Present |

As shown in Table 3 and FIGS. 3 and 4, it can be seen that the medical material according to the present disclosure shows high antithrombogenicity.

From the results described above, it can be seen that the medical material according to the present disclosure has high antithrombogenicity even when being used under severe conditions in which thrombi are easily formed. The medical material according to the present disclosure is particularly useful for a medical apparatus or the like provided with a throttle portion such as a joint portion of a tube which is used under a condition that there is a step on a surface coming into contact with blood, for example.

The detailed description above describes exemplary medical materials and apparatuses. The disclosure is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

1 Tube 1
2 Tube 2
3 Stepped surface
4 Thrombi

What is claimed is:
1. A medical apparatus comprising:
a base material having a stepped surface; and
a coating layer containing a medical material on the surface of the base material, the medical material comprising:
a water-insoluble copolymer comprising:
a repeating unit (A) represented by the following Formula (1):

(1)

wherein in Formula (1), $R^{11}$ is a hydrogen atom or a methyl group and X is represented by the following Formula (1a):

(1a)

wherein in Formula (1a), $R^{12}$ and $R^{13}$ are ethylene groups and Y is an oxygen atom; and
a repeating unit (B) represented by the following Formula (2):

(2)

wherein in Formula (2), $R^{21}$ is a hydrogen atom or a methyl group, $R^{22}$ is an alkylene group having 1 to 4 carbon atoms, and $R^{23}$ is an alkyl group having 1 to 4 carbon atoms,
wherein the water-insoluble copolymer has 6 mole % to 19 mole % of the repeating unit (A) with respect to all constituent units of the copolymer.

2. The medical apparatus according to claim 1, wherein the copolymer has 81 mole % to 94 mole % of the repeating unit (B) with respect to all constituent units of the copolymer.

3. The medical apparatus according to claim 1, wherein the total amount of the repeating unit (A) and the repeating unit (B) is 100 mole % with respect to all constituent units of the copolymer.

4. The medical apparatus according to claim 1, wherein in Formula (1), $R^{11}$ is hydrogen.

5. The medical material apparatus according to claim 1, wherein in Formula (2), $R^{21}$ is hydrogen.

6. The medical apparatus according to claim 1, wherein in Formula (2), $R^{22}$ is a straight or branched-chain alkylene group having 1 to 3 carbon atoms.

7. The medical apparatus according to claim 1, wherein in Formula (2), $R^{23}$ is a straight or branched-chain alkyl group having 1 to 3 carbon atoms.

8. The medical apparatus according to claim 1, wherein the copolymer further comprises a third repeating unit in an amount of less than or equal to 15 mole % with respect to all constituent units of the copolymer.

9. The medical apparatus according to claim 2, wherein in Formula (2), $R^{21}$ is hydrogen, $R^{22}$ is a straight or branched-chain alkylene group having 1 to 3 carbon atoms, and $R^{23}$ is a straight or branched-chain alkyl group having 1 to 3 carbon atoms.

10. The medical apparatus according to claim 9, wherein in Formula (2), $R^{22}$ is an ethylene, and $R^{23}$ is a methylene.

11. The medical apparatus according to claim 10, wherein the total amount of the repeating unit (A) and the repeating unit (B) is 100 mole % with respect to all constituent units of the copolymer.

* * * * *